United States Patent [19]

Kennedy et al.

[11] Patent Number: 5,084,028
[45] Date of Patent: Jan. 28, 1992

[54] NEEDLE COVER AND DISPENSER

[76] Inventors: Michael D. Kennedy, 112 Centre St.; Sanford Kurtz, 21 Newell Rd., both of Brookline, Mass. 02146

[21] Appl. No.: 377,900

[22] Filed: Jul. 10, 1989

[51] Int. Cl.⁵ .............................................. A61M 5/32
[52] U.S. Cl. ...................................... 604/192; 604/263; 128/919; 206/366; 221/303; 221/281
[58] Field of Search ............... 604/192, 263, 187; 206/365, 366; 128/919; 221/191, 193, 194, 195, 196, 303, 306, 281

[56] References Cited

U.S. PATENT DOCUMENTS

| | | | |
|---|---|---|---|
| 2,835,377 | 5/1958 | May et al. | 206/366 |
| 4,014,330 | 3/1977 | Genese | 128/218 |
| 4,105,500 | 8/1978 | Libman et al. | 195/103.5 |
| 4,139,009 | 2/1979 | Alverez | 128/218 |
| 4,142,633 | 3/1979 | Raghavachari et al. | 206/366 |
| 4,171,698 | 10/1979 | Genese | 128/218 |
| 4,315,592 | 2/1982 | Smith | 229/38 |
| 4,375,849 | 3/1983 | Hanifl | 206/366 |
| 4,430,082 | 2/1984 | Schwabacher | 604/263 |
| 4,467,947 | 8/1984 | Minneman | 224/253 |
| 4,559,042 | 12/1985 | Votel | 604/192 |
| 4,596,562 | 6/1986 | Vernon | 604/192 |
| 4,693,708 | 9/1987 | Wanderer et al. | 604/198 |
| 4,695,274 | 9/1987 | Fox | 604/192 |
| 4,702,738 | 10/1987 | Spencer | 604/198 |
| 4,731,059 | 3/1988 | Wanderer et al. | 604/192 |
| 4,775,057 | 10/1988 | Zingeser | 211/133 |
| 4,801,013 | 1/1989 | Bruno | 206/366 |
| 4,836,373 | 6/1989 | Goldman | 206/366 |
| 4,848,569 | 7/1989 | Leishman | 206/365 |
| 4,869,366 | 9/1989 | Bruno | 206/370 |
| 4,890,734 | 1/1990 | Gach | 206/366 |
| 4,917,243 | 4/1990 | Abrams et al. | 206/365 |
| 4,919,264 | 4/1990 | Shinall | 206/210 |
| 4,973,315 | 11/1990 | Sincock | 604/192 |

FOREIGN PATENT DOCUMENTS

| | | | |
|---|---|---|---|
| 2198644 | 6/1988 | United Kingdom | 604/192 |
| 2215215 | 9/1989 | United Kingdom | 604/263 |

Primary Examiner—John D. Yasko
Assistant Examiner—Mark O. Polutta
Attorney, Agent, or Firm—Weingarten, Schurgin, Gagnebin & Hayes

[57] ABSTRACT

An IV, vacutainer, butterfly, or syringe needle cover and dispenser for a plurality of such needle covers that provides individual release of the covers. The dispenser is adapted for attachment to a wall, other surface or a tray. The dispenser is provided with a hinged door which partially covers the bottom needle cover while it allows for the insertion of a needle into that needle cover. The needle cover is provided with gripping surfaces that secure the cover to a needle after needle insertion. The hinged door swings out of the way to allow for the withdrawal from the dispenser of the needle cover attached to a needle. The device insures safe disposal of used needles.

14 Claims, 3 Drawing Sheets

NEEDLE COVER AND DISPENSER

FIELD OF THE INVENTION

The present invention relates to method and apparatus for the safe disposal of used IV, vacutainer, butterfly, or syringe needles and more specifically to a needle cover and needle cover dispenser.

BACKGROUND OF THE INVENTION

The AIDS epidemic as well as other serious diseases have made it imperative that used IV and syringe needles be handled as safely as possible. Accidental pricking with a used needle can be the cause of the spread of serious diseases to health care personnel.

It is thus dangerous to throw away used needles which are not covered. All needles should or must be covered after use and before being placed in disposal containers. In manually replacing covers on needles, there is a high risk of being pricked in the fingers because of the small target area for a successful mating of needle and cover.

SUMMARY OF THE INVENTION

According to the teaching of the present invention a method and apparatus are provided for safely covering used IV, vacutainer, butterfly, or syringe needles without exposure of fingers or other body parts to the dangers of being accidently pricked.

The apparatus of the invention in a preferred embodiment comprises a dispenser filled with needle covers. The dispenser may be attached to a surface such as a wall avoiding the need for handling the dispenser. A used needle is simultaneously inserted into the dispenser and into a needle cover through the hinged door of the holder. The needle is then withdrawn from the dispenser, with the needle cover attached, as the hinged door opens in response to the withdrawal of the needle cover from the dispenser.

Each of the needle covers have cone shaped slots on opposite sides to accomodate needle wings found on IV butterfly needles upon insertion. Small, angled teeth immediately inside the aperture of the needle cover grip the base of the needle to secure it on the needle without impeding insertion. More teeth line the cone shaped slits at opposite sides of the needle cover to grip the wings upon entrance of the needle into the needle cover and retard withdrawal of the needle from the needle cover. The needle covers may be made of a molded plastic or polymer material.

The dispenser stores the covers in a vertical column and may be made of a clear, puncture resistant plastic material through which the needle covers contained within the dispenser may be seen and replaced when the supply gets low.

The dispenser includes a hinged door which partially covers the bottom needle cover in the column. A groove in the base of the door allows insertion of the needle through the door into the cover aperture. Wedge shaped slots in opposite sides of the dispenser, and which are parallel to the base of the hinged door, accomodate the wings to allow complete insertion of the needle into the needle cover. The covers are flattened on the sides so they will fit in the dispenser only with the slots laterally positioned.

BRIEF DESCRIPTION OF THE DRAWING

The invention will be more fully understood from the following solely exemplary detailed description taken in conjunction with the accompanying drawings in which:

FIG. 1B is a front view of the hinged door for the dispenser shown in FIG. 1a;

DESCRIPTION OF THE INVENTION

The invention will be described with reference to an apparatus and method for enabling safe covering and disposal of a used IV or syringe needle.

Figure 1B:
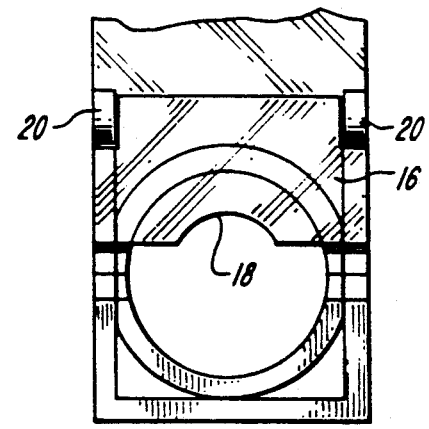
Figure 1A:
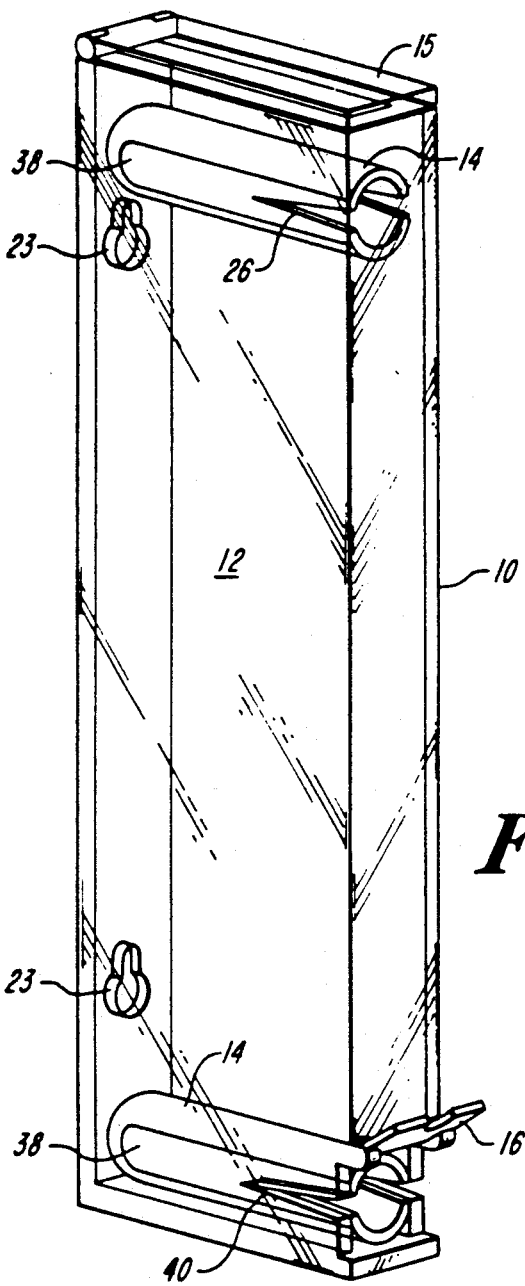
FIG. 1A is a perspective view of a dispenser and cover of the invention.
Figure 1C:
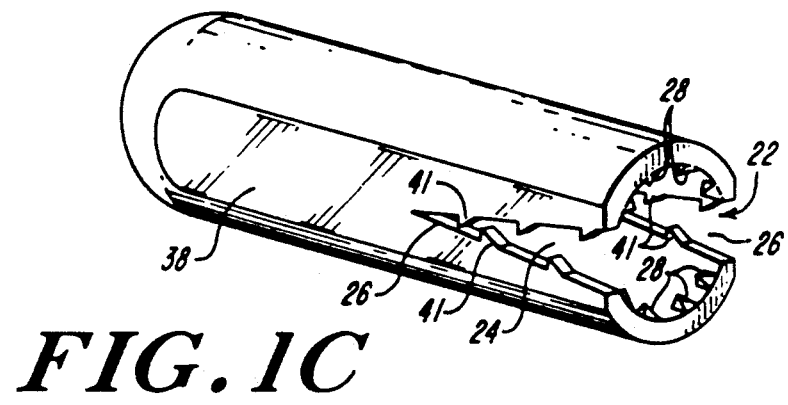
FIG. 1C is a perspective view of a needle cover of the invention.

Referring to FIGS. 1A-1C there is shown the present invention which includes a dispenser 10 having an internal cavity 12 adapted to store a plurality of needle covers 14 and also having a hinged withdrawal door 16 and a hinged upper replenishment door 15. The dispenser 10 may be adapted to hold the needle covers 14 adjacent to one another in a vertical fashion as shown in FIG. 1A.

The hinged door 16 is most preferably located at the bottom of the holder 10 as shown in FIG. 1A. An enlarged view of the hinged door 16 is shown in FIG. 1B. The hinged door 16 comprises a centrally located groove 18 which is shaped to accommodate an IV, vacutainer, butterfly or syringe needle as it is inserted into the bottom cover in the dispenser 10. The hinges 20 allow the hinged door 16 to open outward and away from the dispenser 10 as shown in FIG. 1A for cover withdrawal.

As shown in FIG. 1A, the dispenser 10 has wedge shaped slots 40 located in each side of the dispenser, wider at the location of the door 16, and with an axis parallel to the base of the dispenser 10. These wedge shaped slots 40 accomodate wings 31 (FIG. 2A) of a typical IV or butterfly needle 30.

A perspective view of the needle cover 14 is shown in FIG. 1C. Each needle cover 14 has an internal cavity 24 that accommodates an IV, vacutainer, butterfly or syringe needle and an entrance aperture 22 to the internal cavity 24. As shown in FIG. 1C, an entrance aperture 22 has upper and lower inwardly angled teeth 28 which grip the base of the needle and secure the needle within the cover. The entrance aperture 22 also has wedge shapes slots 26 on opposite sides which accomodate needle wings 31. As shown in FIG. 1C, the wedge shaped slots 26 are lined with small inwardly angled teeth 41 which grip the wings 31 of a needle 30 and retard withdrawal of a needle 30 from the needle cover 14. The slots 26 of the bottom most cover 14 and the slots 40 of the dispenser are aligned to permit the entry of wings 31 on an IV or butterfly needle.

The needle covers 14 have flat, opposite sides 38, as shown in FIGS. 1A and 1C, and diameters elsewhere greater than the inner width of the dispenser 10 to insure proper orientation of the needle covers 14 as they are dropped into position in the dispenser 10. Proper orientation is particularly important when the needle 30 has wings 31 which must be inserted into the cone shaped slots 26 of the needle cover 14.

Figure 3:
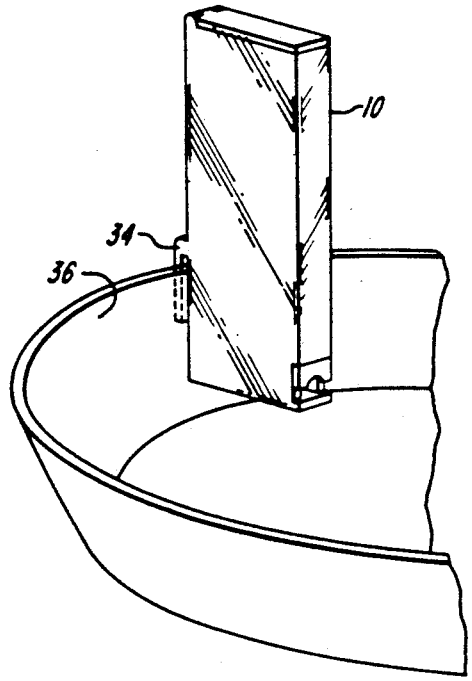
FIG. 3 is a perspective view of the invention as it may appear when removably attached to a portable tray.
Figure 2A:
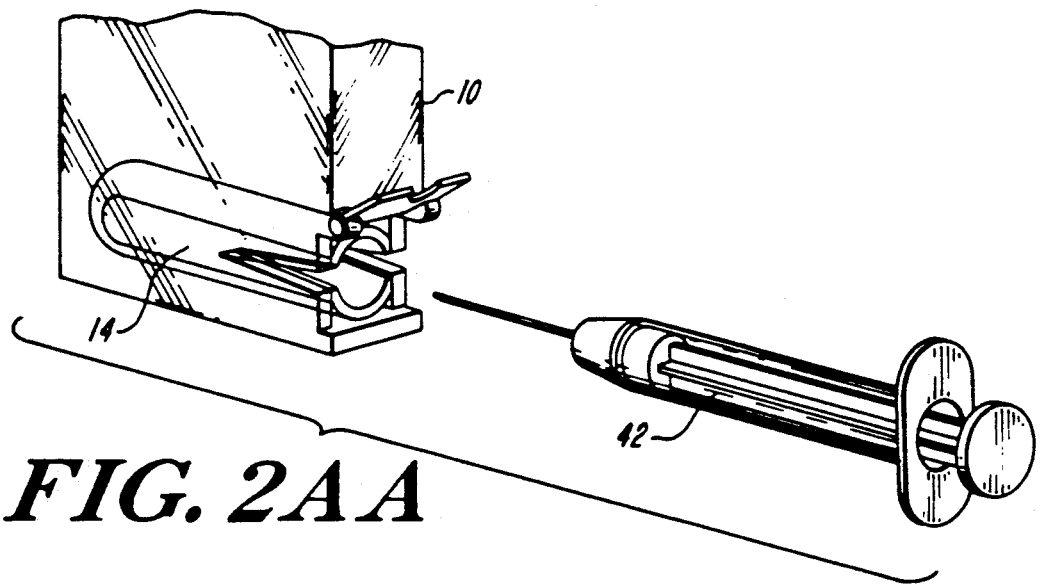
Figure 2B:
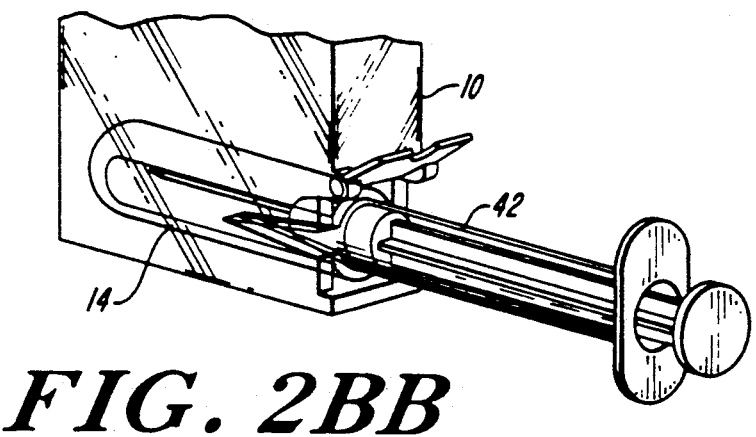
Figure 2C:
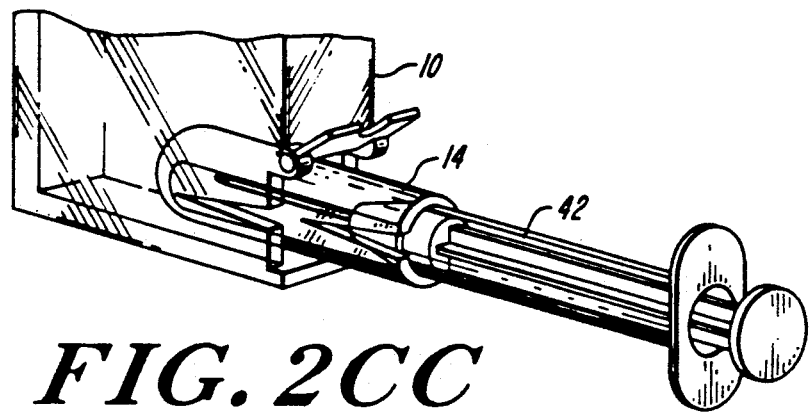

Securing holes 23 allow the dispenser 10 to be mounted to a wall or otherwise secured to avoid having to handle the dispenser cover and thus avoid pricking. As shown in FIG. 3, a removable clip 34 may be secured to the back of the dispenser to be used to attach it to the edge rim of a tray 36 or other portable surface.

Figure 2A:
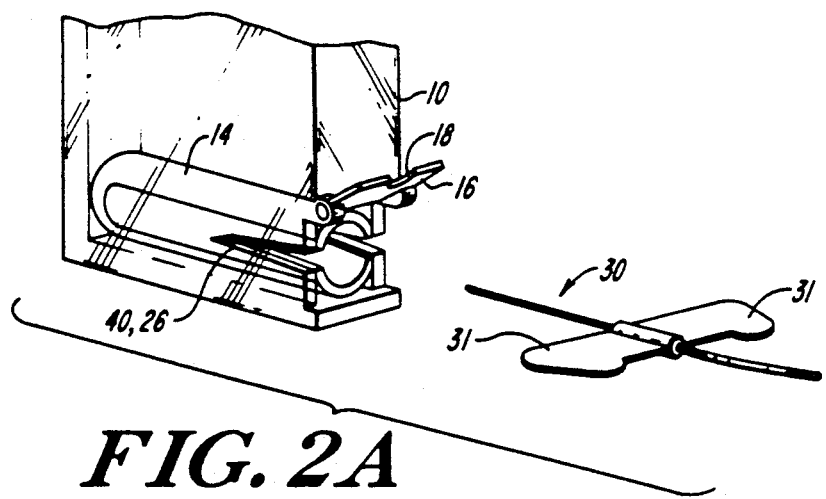
FIGS. 2A and 2AA are perspective views of an IV needle, having wings, and syringe respectively in the process of entering the dispenser.
Figure 2B:
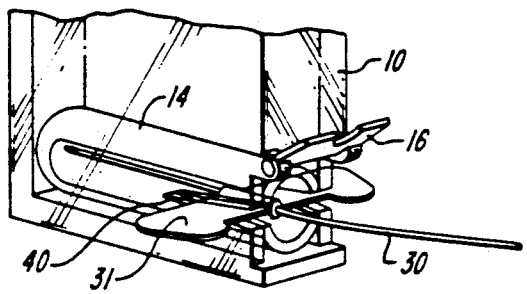
FIGS. 2B and 2BB are perspective views of the IV needle and syringe respectively secured within a needle cover inside the dispenser.
Figure 2C:
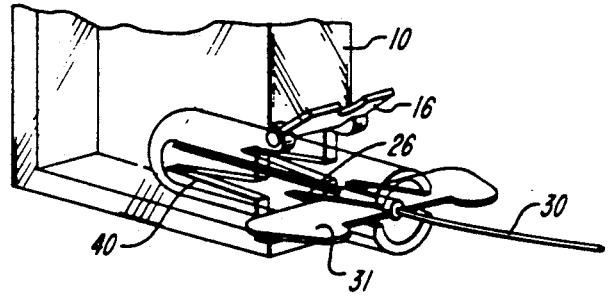
FIGS. 2C and 2CC are perspective views of the IV needle and syringe respectively being withdrawn from the dispenser with a needle cover attached.

Referring now to FIGS. 2A-2C the steps in the use of the invention to cover a needle are shown. A needle 30 having wings 31 is inserted into the dispenser 10 and bottom cover 14 guided by the groove 18, in hinged door 16 which is located at the bottom of the needle dispenser 10 along with the dispenser slots 40 and cover slots 26. In FIG. 2B the needle 30 has been fully inserted into the dispenser 10 and into the needle cover 14 with the wings 31 in the slots 40 and gripped by teeth 41 and slots 26. In FIG. 2C the needle 30 is being withdrawn from dispenser 10, the hinged door 16, raised by the cover 14 as it is removed with a needle attached.

The above description has referred specifically to features which accomodate the use of an IV or butterfly needle which has wings. However, the invention is also suitable for use with a vacutainer or syringe needle which does not have wings. If such use is to be exclusive, the slots 40 and 26 may be dispensed with.

FIGS. 2AA, 2BB and 2CC show the same steps repeated with a syringe 42 in place of the needle 30, being inserted into the cover 14. The slots 40 and 26 have been retained in its views of FIGS. 2AA-2CC for completeness.

The invention is not to be limited by what has been particularly shown and described except as indicated by the appended claims.

What is claimed is:

1. Apparatus for enabling safe covering of a needle comprising:
   a needle cover holder defining a cavity adapted to store a plurality of needle covers; and
   a plurality of needle covers disposed within said cavity of said holder, wherein each of said plurality of needle covers defines an internal cover cavity and a cover entrance aperture to said cover cavity, the cover aperture of each of said needle covers allowing needle insertion into said needle cover cavity and retarding removal of an inserted needle from said needle cover cavity,
   said needle cover holder further comprising a holder aperture means at a predetermined location in said cover holder for allowing insertion of a needle into a cover cavity of a cover in said plurality of stored covers and permitting withdrawal of a needle cover from said needle cover holder with that needle attached.

2. The apparatus of claim 1 wherein;
   said aperture of said needle cover includes side portions and said needle cover holder has corresponding slots aligned with the side portion of said needle cover aperture when said needle cover is adjacent said predetermined location.

3. The apparatus of claim 1 wherein said holder aperture means associated with said holder for allowing insertion of a needle into said holder comprises a hinged door having a groove at the center of its base which guides the passage of a needle into a cover cavity.

4. The apparatus of claim 1 wherein said cover aperture has a diameter, which is slightly greater than the diameter of a portion of the needle which allows for the entry of the needle into said opening.

5. The apparatus of claim 1 wherein said needle cover has an outer wall, the opposite sides which are flat to allow for proper orientation said needle cover within said needle cover holder.

6. The apparatus of claim 4 wherein said needle cover aperture comprises means for retarding withdrawal of an inserted needle from said needle cover comprising teeth in said aperture which allow for a gripping of the needle within said aperture of said needle cover.

7. The apparatus of claim 1 wherein said needle cover has longitudinally directed wedge shaped slots on opposite sides of said needle cover, tapering in from said cover aperture to accommodate wings on a needle.

8. The apparatus of claim 7 wherein said slots have teeth which allow for wing gripping to retard withdrawal of the needle having wings from the needle cover.

9. The apparatus of claim 1 wherein said holder includes a vertical compartment for storing said needle covers vertically and said predetermined holder location for allowing insertion of a needle is at the bottom of said holder.

10. The apparatus of claim 1 wherein said holder has wedge shaped slots parallel to the base of said holder and on opposite sides of said holder for allowing insertion of a needle having wings into said needle cover.

11. The apparatus of claim 1 wherein said holder has means for removably attaching said holder to a surface.

12. The apparatus of claim 1 wherein said holder is made of a clear plastic material.

13. The apparatus of claim 1 wherein said needle covers are molded of a plastic material.

14. The apparatus of claim 1 wherein said entrance aperture to said cavity includes a tapered aperture in the side walls of said needle cover.

* * * * *